(12) United States Patent
Hsieh et al.

(10) Patent No.: US 9,180,340 B2
(45) Date of Patent: Nov. 10, 2015

(54) RESPIRATORY TRAINING ASSEMBLY

(71) Applicant: E-Top Union Inc., New Taipei (TW)

(72) Inventors: Meng Tsung Hsieh, New Taipei (TW); Chih-Wei Feng, Taipei (TW)

(73) Assignee: E-Top Union Inc., New Taipei (TW)

( * ) Notice: Subject to any disclaimer, the term of this patent is extended or adjusted under 35 U.S.C. 154(b) by 306 days.

(21) Appl. No.: 13/854,179

(22) Filed: Apr. 1, 2013

(65) Prior Publication Data

US 2014/0135176 A1 May 15, 2014

(30) Foreign Application Priority Data

Nov. 12, 2012 (TW) .............................. 101221807 U

(51) Int. Cl.

| A63B 23/18 | (2006.01) |
|---|---|
| A61B 5/08 | (2006.01) |
| A61B 5/091 | (2006.01) |
| A63B 21/008 | (2006.01) |
| A63B 21/00 | (2006.01) |
| A61B 5/087 | (2006.01) |
| F16K 15/14 | (2006.01) |
| A61M 39/24 | (2006.01) |

(52) U.S. Cl.
CPC ................. *A63B 23/18* (2013.01); *A61B 5/091* (2013.01); *A63B 21/00069* (2013.01); *A63B 21/0085* (2013.01); *A61B 5/08* (2013.01); *A61B 5/0875* (2013.01); *A61M 2039/2453* (2013.01); *F16K 15/141* (2013.01)

(58) Field of Classification Search
CPC .............. A63B 23/18; A63B 21/0085; A63B 21/00069; A61B 5/0875; A61B 5/091; B01D 2201/167; F16K 24/042; F16K 15/141; A61M 2039/2453

USPC ......................... 482/13; 600/529–543; 55/420
See application file for complete search history.

(56) References Cited

U.S. PATENT DOCUMENTS

| 1,392,700 A | * | 10/1921 | Oyen ............................... 482/13 |
|---|---|---|---|
| 2,362,240 A | * | 11/1944 | Bonilla .................... 128/201.11 |
| 2,538,662 A | * | 1/1951 | Abbott .......................... 604/247 |
| 3,601,152 A | * | 8/1971 | Kenworthy .................... 137/843 |
| 4,025,070 A | * | 5/1977 | McGill et al. ................... 482/13 |
| 4,114,608 A | * | 9/1978 | Russo ............................ 600/538 |
| 4,143,872 A | * | 3/1979 | Havstad et al. ................... 482/8 |

(Continued)

FOREIGN PATENT DOCUMENTS

| WO | WO 2009031018 A2 * | 3/2009 | ............ A61M 39/24 |
|---|---|---|---|

*Primary Examiner* — Oren Ginsberg
*Assistant Examiner* — Joshua Lee
(74) *Attorney, Agent, or Firm* — Alan D. Kamrath; Kamrath IP Lawfirm, P.A.

(57) ABSTRACT

A respiratory training assembly has a main body, an expiratory training device mounted in the main body and a handle formed on the main body. The main body has a volume barrel, an inspiratory training device, an air channel and an output-input entrance. The inspiratory training device is mounted movably in the volume barrel and has a floating element. The air channel is formed on the main body, communicates with the volume barrel, and has a check valve. The output-input entrance is formed in the main body and communicates with the air channel. In use, the inspiratory flow path and the expiratory flow path of the respiratory training assembly are separated to prevent pollution from the patient's saliva. Additionally, the expiratory training device can be adjusted according to the patient's requirement to improve the training result.

5 Claims, 9 Drawing Sheets

(56) References Cited

U.S. PATENT DOCUMENTS

| | | | |
|---|---|---|---|
| 4,207,884 A * | 6/1980 | Isaacson | 128/200.24 |
| 4,231,375 A * | 11/1980 | Boehringer et al. | 600/538 |
| 4,259,951 A * | 4/1981 | Chernack et al. | 128/200.14 |
| 4,284,083 A * | 8/1981 | Lester | 600/538 |
| 4,299,236 A * | 11/1981 | Poirier | 600/541 |
| 4,391,283 A * | 7/1983 | Sharpless et al. | 600/538 |
| 4,444,202 A * | 4/1984 | Rubin et al. | 600/538 |
| 4,499,905 A * | 2/1985 | Greenberg et al. | 600/540 |
| D319,880 S * | 9/1991 | Tapolcai | D24/164 |
| 5,431,154 A * | 7/1995 | Seigel et al. | 128/200.14 |
| 5,765,553 A * | 6/1998 | Richards et al. | 128/203.29 |
| 5,984,873 A * | 11/1999 | Crumb et al. | 600/538 |
| 5,992,462 A * | 11/1999 | Atkinson et al. | 137/854 |
| 6,083,141 A * | 7/2000 | Hougen | 482/13 |
| 6,191,497 B1 * | 2/2001 | Wickstead et al. | 307/11 |
| 6,238,353 B1 * | 5/2001 | Weinstein et al. | 600/540 |
| 6,659,100 B2 * | 12/2003 | O'Rourke | 128/200.21 |
| 6,726,598 B1 * | 4/2004 | Jarvis et al. | 482/13 |
| 6,988,510 B2 * | 1/2006 | Enerson | 137/533.31 |
| 2002/0104531 A1 * | 8/2002 | Malone | 128/200.23 |
| 2002/0151813 A1 * | 10/2002 | Niles et al. | 600/532 |
| 2002/0162560 A1 * | 11/2002 | Rogacki | 128/898 |
| 2003/0140925 A1 * | 7/2003 | Sapienza et al. | 128/205.24 |

\* cited by examiner

US 9,180,340 B2

RESPIRATORY TRAINING ASSEMBLY

BACKGROUND OF THE INVENTION

1. Field of the Invention

The present invention relates to a respiratory training assembly and, more particularly, to a respiratory training assembly that can be used to train the volume of patient's lung after surgery and that can prevent the expired air from flowing with the inhaled air to pollute the respiratory training assembly.

2. Description of Related Art

With changes in diet and with environment pollutions, ratios of respiratory organs surgery and cardiovascular surgery have increased year by year. When patients were anesthetized in a respiratory organs surgery or a cardiovascular surgery, the lung function of the patient will be influenced and reduced after the operation. Therefore, the patient needs to strengthen the respiratory muscles by deep breath training. The volume of the patient's lung may be promoted and back to normal by training inspiratory strength with a conventional respiratory training assembly. Conventional respiratory training assemblies can be broadly classified into a floating-disc type, a ball-type, a sport-type, an electrical-type, an inhalation hybrid-type, a vane-type and a mouth-type. Different respiratory training assemblies can provide different training results to the patient's lung, but all of the conventional respiratory training assemblies have the same problem during use. New patients tend to blow instead of suck when they use the conventional respiratory training assemblies the first time, which let saliva, mouth water or sputum of the patient blow into and pollute the channel and a chamber of the conventional respiratory training assembly. The accuracy of the respiratory training result may also be affected, since the weight of a floating element inside the chamber was changed by the patient's saliva, mouth water or sputum. The respiratory training assembly polluted by saliva, mouth water or sputum also enhances disease infecting.

In addition, the conventional respiratory training assembly can only be used for training inspiratory muscles and volume of the patient, and is not able to be used for expiration function improvement of the patient.

To overcome the shortcomings, the present invention provides a respiratory training assembly to mitigate or obviate the aforementioned problems.

SUMMARY OF THE INVENTION

The main objective of the present invention is to provide a respiratory training assembly that can be used to train the patient's lung volume after surgery and that can prevent the expired air from flowing with the inhaled air to pollute the respiratory training assembly.

The respiratory training assembly has a main body, an expiratory training device mounted in the main body and a handle formed on the main body. The main body has a volume barrel, an inspiratory training device, an air channel and an output-input entrance. The inspiratory training device is mounted movably in the volume barrel and has a floating element. The air channel is formed on the main body, communicates with the volume barrel, and has a check valve. The output-input entrance is formed in the main body and communicates with the air drainage channel. In use, the inspiratory flow path and the expiratory flow path of the respiratory training assembly are separated and isolated, and this prevents the patient's saliva from polluting the floating element. Additionally, the expiratory training device can be adjusted according to the patient's need to provide a preferred training effect.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
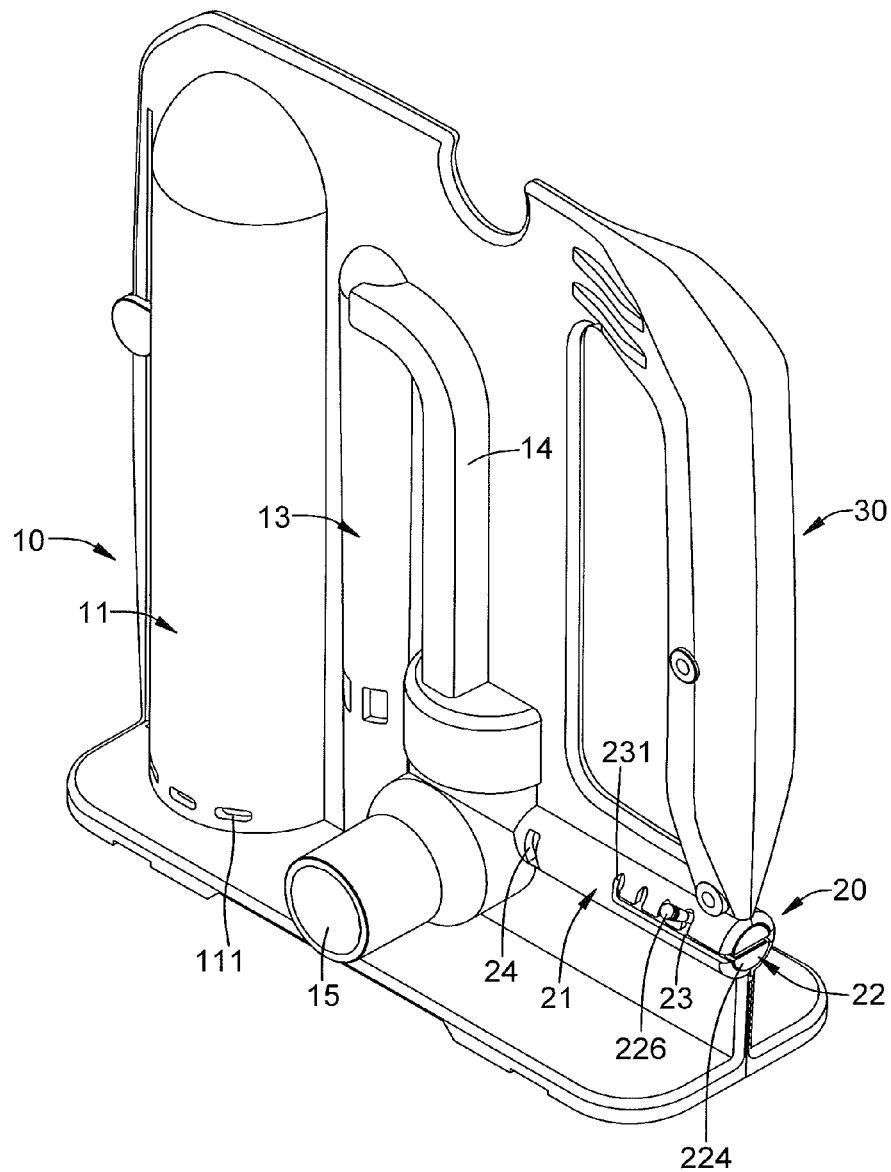
FIG. 1 is a perspective view of a respiratory training assembly in accordance with the present invention.
Figure 2:
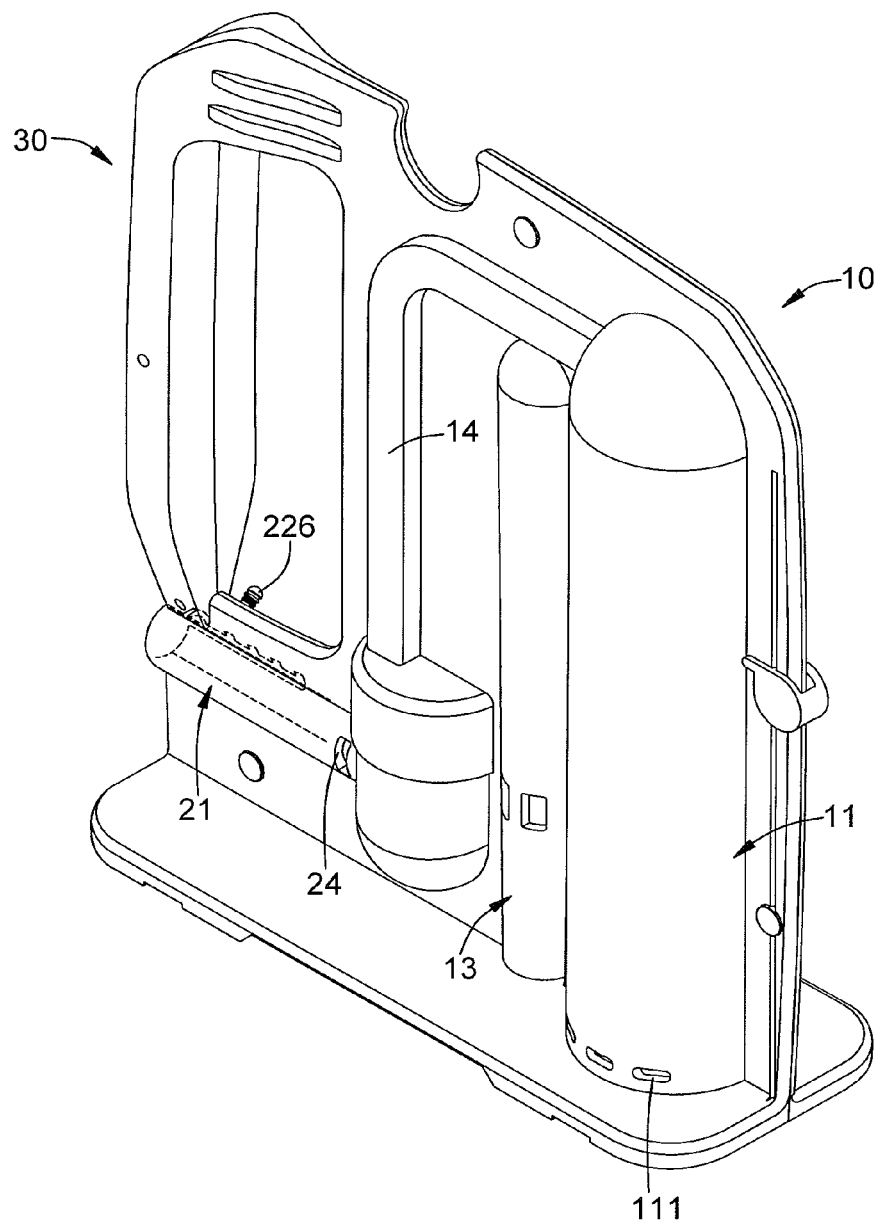
FIG. 2 is another perspective view of a respiratory training assembly in accordance with the present invention.
Figure 3:
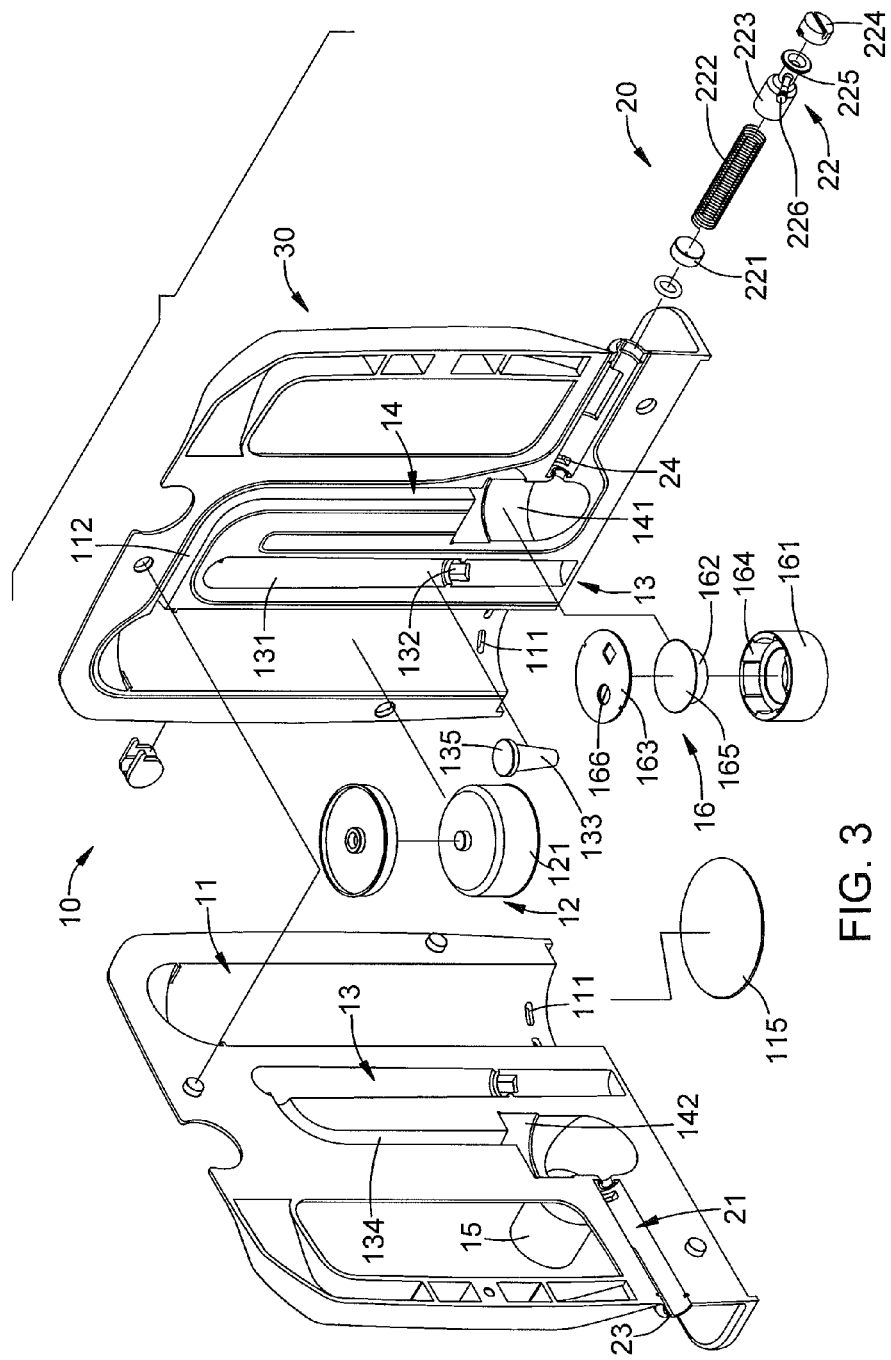
FIG. 3 is an exploded perspective view of the respiratory training assembly in FIG. 1.

With reference to FIGS. 1 to 3, a respiratory training assembly in accordance with the present invention has a main body 10, an expiratory training device 20 and a handle 30. The expiratory training device 20 and the handle 30 are connected to the main body 10.

The main body 10 has a volume barrel 11, an inspiratory training device 12, an auxiliary indicating device 13, an air channel 14 and an output-input entrance 15. The volume barrel 11 may be a partially or completely translucent cylinder and has a top, a bottom, an external surface, a chamber, a cross section, a diameter, at least one through hole 111 and an air outlet hole 112. The at least one through hole 111 is formed through the external surface of the volume barrel 12 near the bottom of the volume barrel 11 and communicates with the chamber of the volume barrel 11. The air outlet hole 112 is formed through the external surface of the volume barrel 11 near the top of the volume barrel 11 and communicates with the chamber of the volume barrel 11. Preferably, the volume barrel 11 in the present invention is a completely translucent cylinder, the top of the volume barrel 11 is a closed type, and the bottom of the volume barrel 11 is an open type. The volume barrel 11 has multiple through holes 111 formed through the external surface of the volume barrel 11 around the volume barrel 11 at intervals.

The inspiratory training device 12 is mounted movably in the volume barrel 11 and has a floating element 121. The floating element 121 is mounted movably in the chamber of the volume barrel 11 and has a cross section corresponding to the cross section of the volume barrel 11 to enable the floating element 121 to move upwardly or downwardly relative to the volume barrel 11. Thus, a user or a patient may know his inspiratory lung volume according to the height of the floating element 121 relative to the volume barrel 11 during training. In the present invention, the volume barrel 11 is mounted by two half-casings to mount the floating element 121 in the chamber of the volume barrel 11. When the air in the chamber of the volume barrel 11 is drawn out of the volume barrel 11 via the air outlet hole 112 by a user or a patient, the air outside the volume barrel 11 can flow into the chamber of the volume barrel 11 via the at least one through hole 111 below the floating element 121. Then, the floating element 121 in the chamber of the volume barrel 11 will be moved upwardly relative to the volume barrel by a suction force. Further, the opened bottom of the volume barrel 11 may be sealed with a sealing sheet 115 after the volume barrel 11 is assembled.

The auxiliary indicating device 13 is formed on the main body 10 and has an indicating channel 131, an engaging recess 132 and an indicating element 133. The indicating channel 131 is formed on the main body 10 parallel to the volume barrel 11 and has a top end, a bottom end, an internal surface, a diameter and a drainage branch 134. The drainage branch 134 is formed on and protrudes downwardly from the top end of the indicating channel 131 and communicates with the indicating channel 131. Preferably, the indicating channel 131 is a flexible tube or is integrally formed with the main body 10 as a single piece. In the present invention, the diameter of the indicating channel 131 is smaller than the diameter of the volume barrel 11. The engaging recess 132 is formed in or partially protrudes from the internal surface of the indicating channel 131 near the bottom end of the indicating channel 131. The indicating element 133 is movably mounted in the indicating channel 131, selectively abuts against and holds in the engaging recess 132 and has a top, a bottom, a width and an annular flange 135. The indicating element 133 may be a cone-like cylinder, and the width of the indicating element 133 is reduced from the top to the bottom of the indicating element 133. The annular flange 135 is formed around the top of the indicating element 133 and selectively abuts against and holds in the engaging recess 132.

The air channel 14 is formed on the main body 10, communicates with the chamber of the volume barrel 11 via the air outlet hole 112 and has an upper end, a lower end, an outlet 141 and a mounting recess 142. The upper end of the air channel 14 is connected to and communicates with the air outlet hole 112 of the volume barrel 11. The outlet 141 is formed on the lower end of the air channel 14 in the main body 10. The mounting recess 142 is enlarged, is formed in the air channel 14 between the outlet 141 and the lower end of the air channel 14, and communicates with the outlet 141 and the air channel 14. Preferably, the air channel 14 is a flexible tube or is formed with the main body 10 as a single piece beside the indicating channel 131.

Furthermore, the main body 10 has a check valve 16 mounted in the air channel 14 and has a valve ring 161, a floating mount 162 and a cover panel 163. The valve ring 161 is hollow, is mounted in the mounting recess 142, communicates with the air channel 14 and has a top edge, an internal surface and at least one hollow section 164. The at least one hollow section 164 is formed in the internal surface of the valve ring 161 and is formed through the top edge of the valve ring 161. The floating mount 162 is movably mounted in the valve ring 161 and has a top and a retaining board 165. The retaining board 165 is formed on and protrudes from the top of the floating mount 162. The cover panel 163 is mounted in the mounting recess 142, is covered around the top of the valve ring 161 and has at least one gas hole 166. The at least one gas hole 166 is formed through the cover panel 163 and communicates with the air channel 14, the mounting recess 142 and the at least one hollow section 164 of the valve ring 161.

When the floating mount 162 is moved upwardly from the at least one hollow section 164 of the valve ring 161, the retaining board 165 of the floating mount 162 may abut the cover panel 163 and seal the at least one gas hole 166. Thus, air flow cannot flow into the air channel 14 via the at least one hollow section 164 of the valve ring 161, and the patient's saliva will not flow into the volume barrel 11 to pollute the volume barrel 11. In the other way, when the floating mount 162 is mounted in the valve ring 161, the retaining board 165 is separated from the cover panel 163 and is able to seal the at least one gas hole 166. Then, air can flow into the air channel 14 through the at least one hollow section 164 of the valve ring 161.

Figure 4:
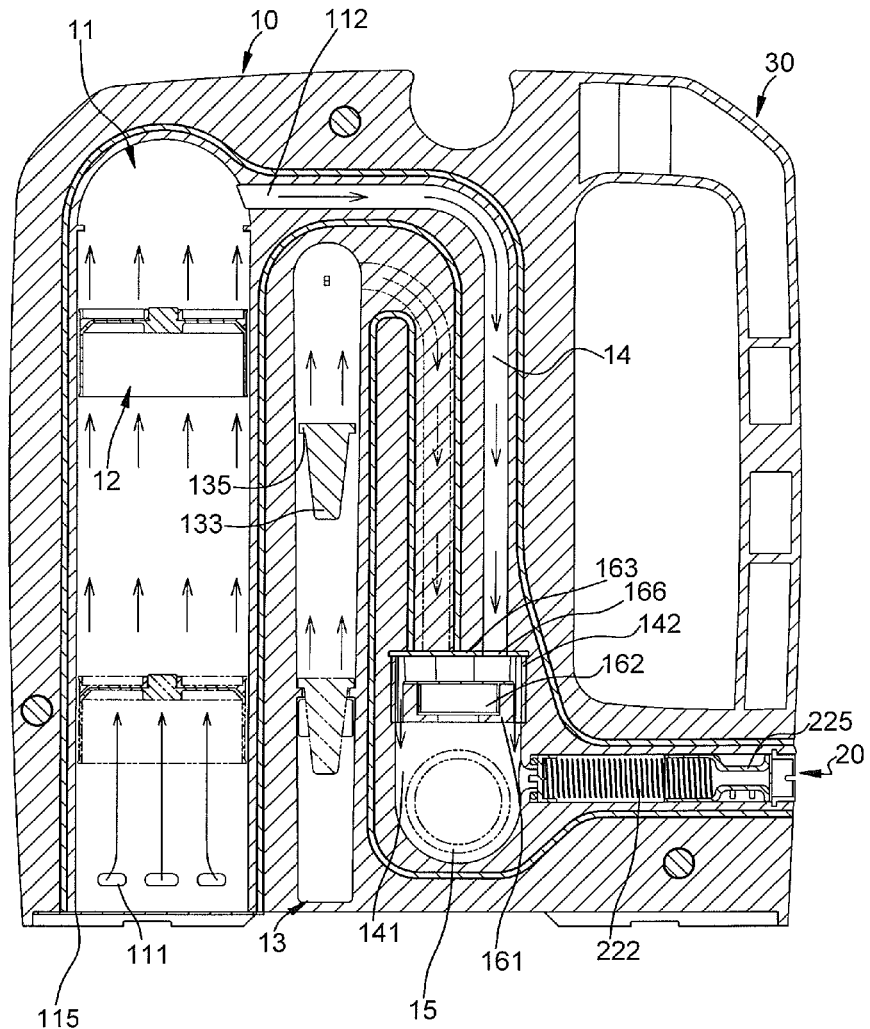
FIG. 4 is an operational cross sectional side view of the respiratory training assembly in FIG. 1 in an inspiratory condition.

The output-input entrance 15 is formed in the main body 10 and communicates with the outlet 141 of the air channel 14. In use, when a patient inhales air from the output-input entrance 15, air in the chamber of the volume barrel 11 will be directed and flows into the output-input entrance 15 through the air outlet hole 112, the air channel 14 and check valve 16 sequentially. With reference to FIG. 4, when the patient inhales air from the output-input entrance 15 as described above, the floating mount 162 is mounted in the valve ring 161 without sealing the at least one gas hole 166 of the cover panel 163. Thus, air in the chamber of the volume barrel 11 will be breathed in the patient's lung for training the volume of the lung and the related muscles.

Figure 5:
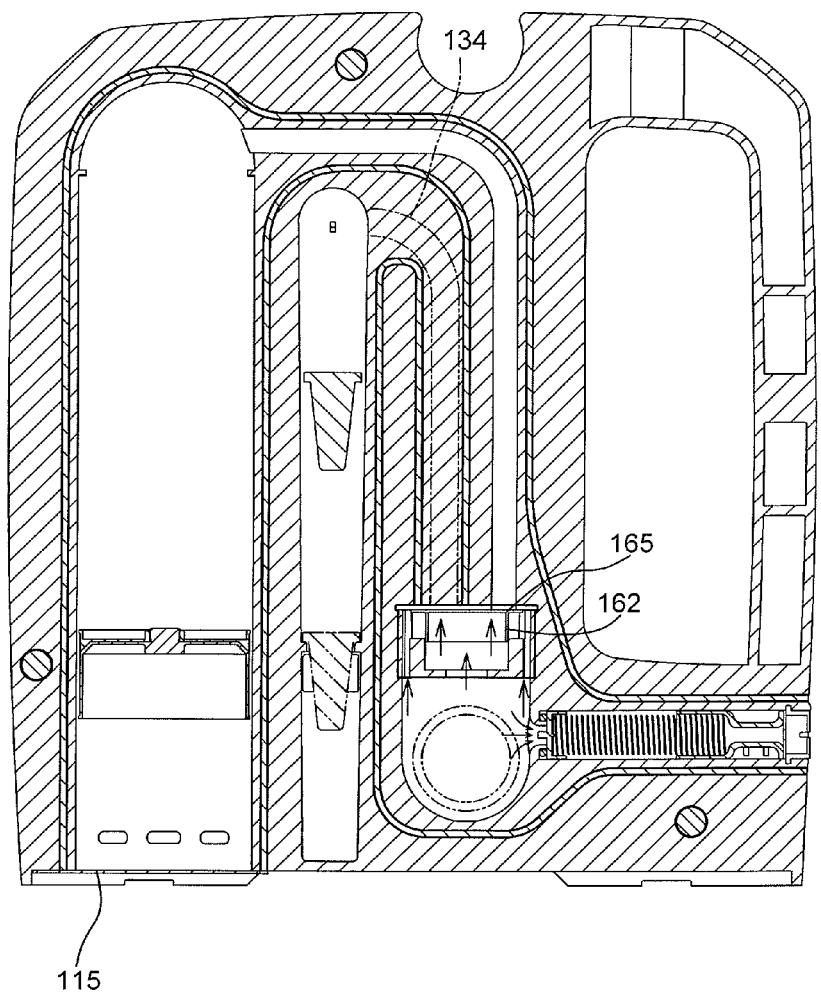
FIG. 5 is an operational cross sectional side view of the respiratory training assembly in FIG. 1 in an expiratory condition.
Figure 6:
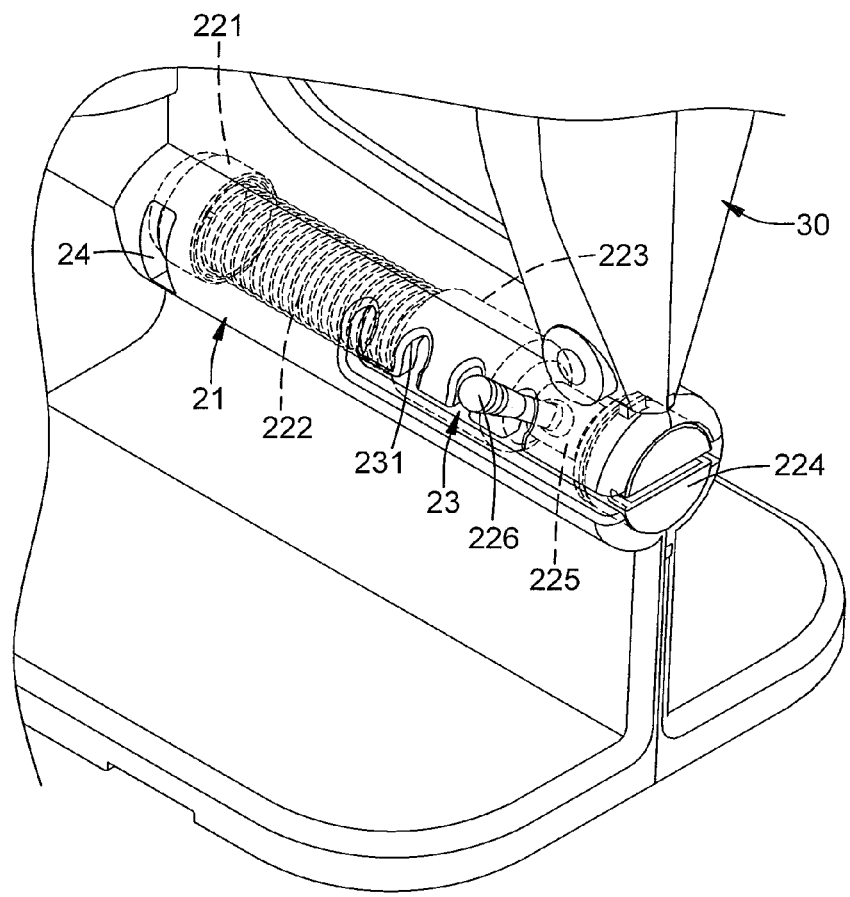
FIG. 6 is an enlarged perspective view of an expiratory training device of the respiratory training assembly in FIG. 1.
Figure 7:
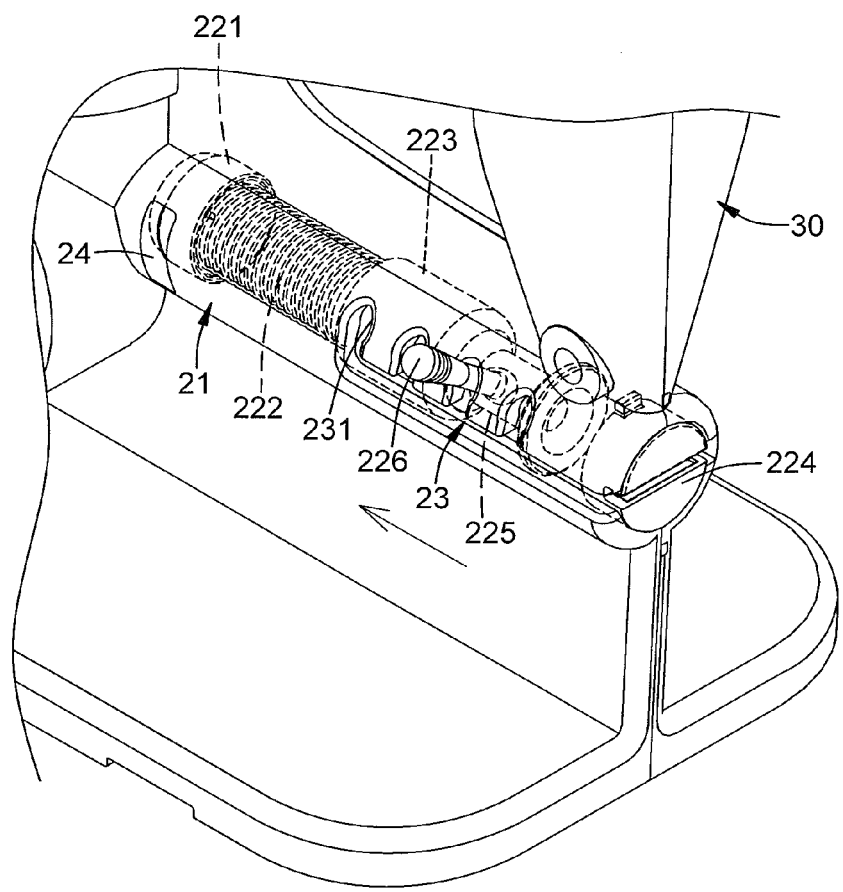
FIG. 7 is another enlarged perspective view of the expiratory training device of the respiratory training assembly in FIG. 1.
Figure 8:
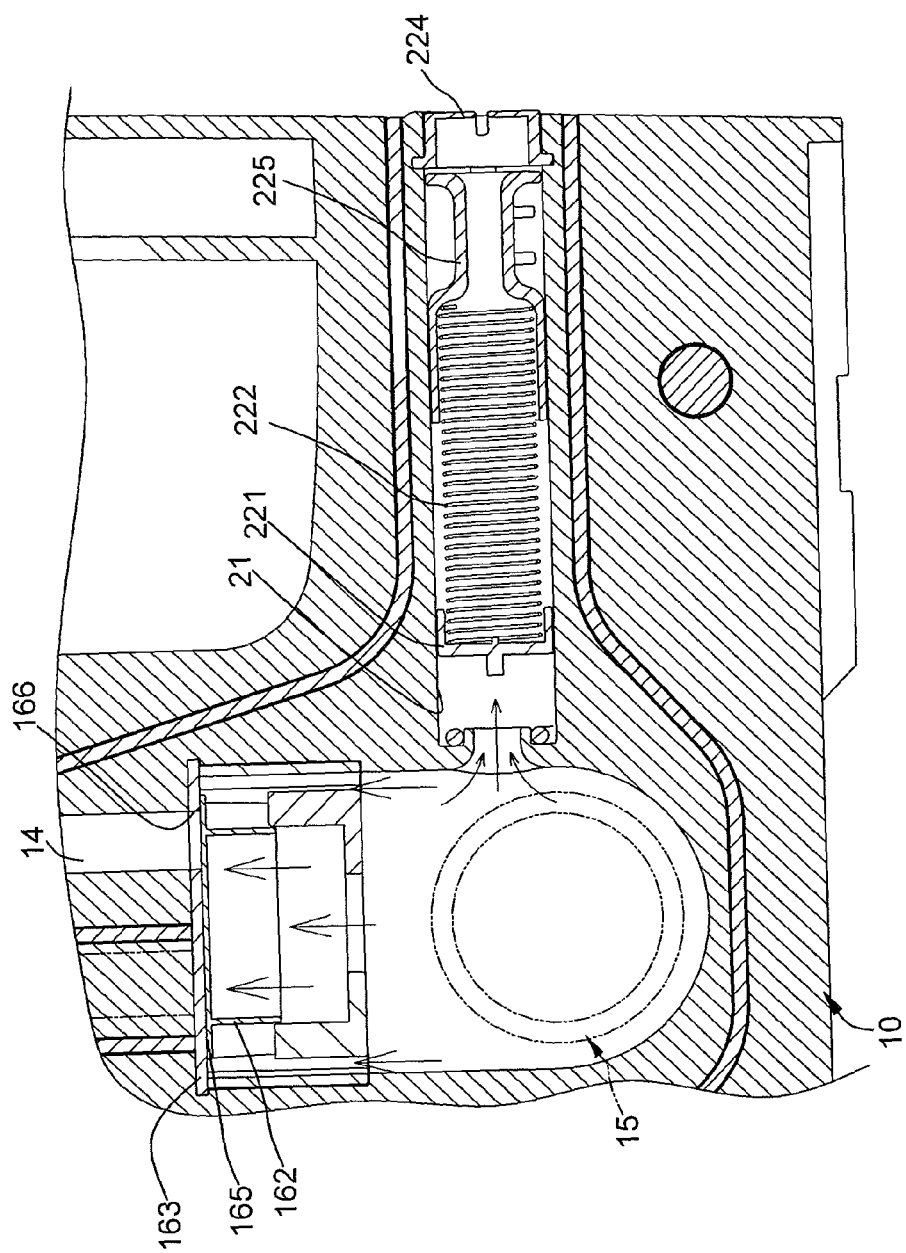
FIG. 8 is an enlarged and operational cross sectional side view of the respiratory training assembly in FIG. 1 in an expiratory condition.
Figure 9:
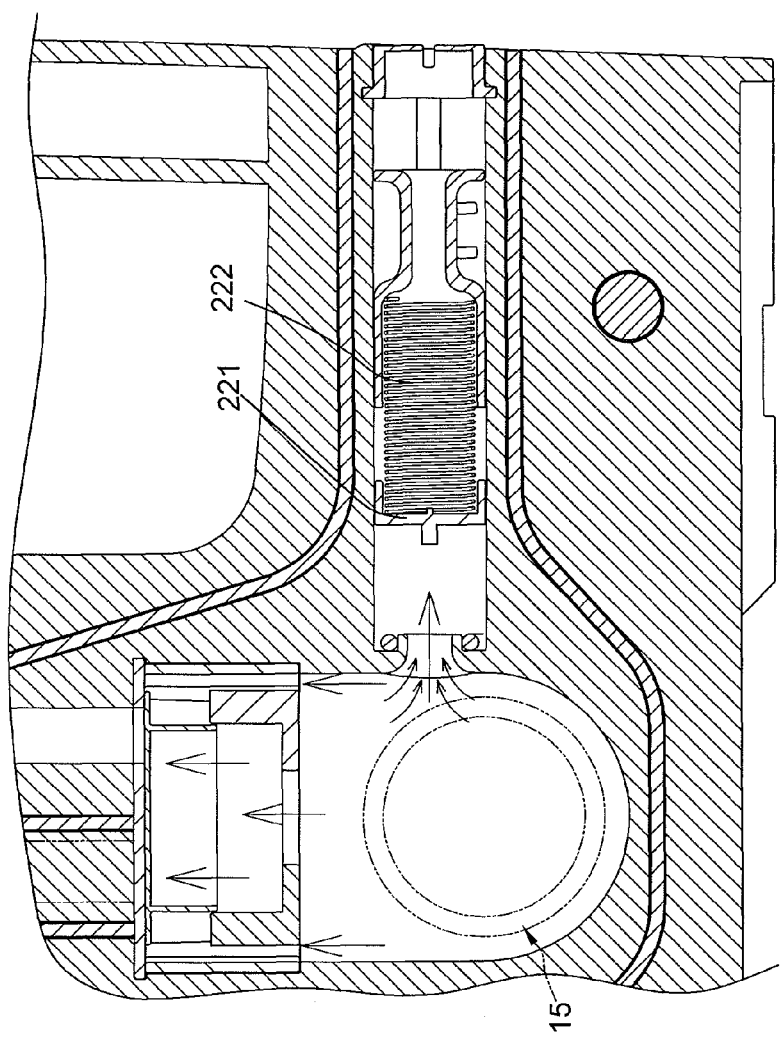
FIG. 9 is another enlarged and operational cross sectional side view of the respiratory training assembly in FIG. 1 in an expiratory condition.

With referenced to FIG. 5, when the patient blows air into the output-input entrance 15, the floating mount 162 will be moved upwardly relative to the valve ring 161, and the retaining board 165 will abut and seal the at least one gas hole 166 of the cover panel 163. Thus, the air from the patient's mouth cannot flow into the air channel 14. Consequently, when the user or the patient uses the respiratory training assembly in accordance with the present invention, the inhaled air will not flow through the check valve 16 that is mounted in the mounting recess 142, and mouth water is also stopped to prevent the polluting problem in the conventional respiratory training assembly.

With referenced to FIGS. 5 to 9, the expiratory training device 20 is mounted in the main body 10 between the output-input entrance 15 and the check valve 16, communicates with the air channel 14 and is able to adjust the flow resistance when the user or patient blows air. The expiratory training device 20 may have a mechanical indicating structure or an electrical indicating structure for indicating the flow resistance and expiratory training result of the patient. In the present embodiment, the expiratory training device 20 has an expiratory body 21 and a pressure adjuster 22. The expiratory body 21 is tubular, is formed with the main body 10 and communicates with the air channel 14. The pressure adjuster 22 is mounted movably in the expiratory body 21 and is used to adjust the air expired pressure. Preferably, the pressure adjuster 22 may be, but is not limited to, a rotating knob, an adjusting valve or a device that can be used to exert pressure upon the air drain channel 14. The indicating structure may be connected to and communicated with an air outlet of the expiratory body 21, and air from the expiratory training device 20 may be directed into the indicating structure and shows an expiratory strength of the patient.

In the present invention, the expiratory body 21 has an external surface, a forming end, a mounting end, at least one elongated slot 23 and at least one leaking hole 24. The forming end of the expiratory body 21 is formed with the main body 10 and communicates with the outlet 141 of the air channel 14. The at least one elongated slot 23 is formed axially through the external surface of the expiratory body 21, and each of the at least one elongated slot 23 has multiple holding recesses 231 formed through the external surface of the expiratory body 21 separately and communicating with the at least one elongated slot 23. The at least one leaking hole 24 is formed through the external surface of the expiratory body 21 near the forming end of the expiratory body 21 and communicates with the air channel 14 via the forming end of the expiratory body 21.

The pressure adjuster 22 has a controlling slice 221, an elastic element 222, an adjusting element 223 and a holding cap 224. The controlling slice 221 is movably mounted in the expiratory body 21 near the forming end of the expiratory body 21. The elastic element 222 may be a spring or a reed, is mounted in the expiratory body 21 and abuts against the controlling slice 221 to provide a pushing force to the controlling slice 221 to move toward the forming end of the expiratory body 21.

The adjusting element 223 is movably mounted in the expiratory body 21, abuts against the elastic element 222 and has an abutting end, a connecting shaft 225 and an engaging rod 226. The abutting end of the adjusting element 223 abuts against the elastic element 222 to provide a pushing force to the elastic element 222 and the controlling slice 221 to move toward the forming end of the expiratory body 21. The connecting shaft 225 is formed axially on and protrudes from the abutting end of the adjusting element 223 opposite to the elastic element 222 and has an external surface. The engaging rod 226 is radially formed on and protrudes from the external surface of the connecting shaft 225 and has an engaging end extending into the at least one elongated slot 23 and engaging one of the holding recesses 231 of the at least one elongated slot 23 to hold the adjusting element 223 securely with the expiratory body 21.

The holding cap 224 is mounted securely in the mounting end of the expiratory body 21 to hold the adjusting element 223, the elastic element 222 and the controlling slice 221 securely in expiratory body 21.

The expiratory indicating structure is formed on the expiratory body 21 near the at least one leaking hole 24, and the expiratory indicating structure has a tube and a floating ball movably mounted in the tube. The height of the floating ball in the tube may correspond to the strength of the airflow blown by the patient. Thus, the patient may know the training result of the expiratory training process.

In use, when the patient blows air into the output-input entrance 15, the expired air will be directed into the expiratory body 21 via the forming end of the expiratory body 21, since the check valve 16 closes a pathway of air into the air channel 14. In addition, the position of the adjusting element 223 is held by locating the engaging rod 226 in one of the corresponding holding recesses 231 of the elongated slots 23, and a pressure of the elastic element 222 put on the controlling slice 221 may thus be adjustable from locating the engaging rod 226 in the holding recesses 231. The sealing force of the controlling slice 221 is then adjustable accordingly.

The handle 30 is formed on the main body 10 and may be formed with the main body 10 as a single piece. In addition, the main body 10 and the handle 30 may be composed by two half-casings and can be formed by two corresponding molds.

Additionally, the respiratory training assembly in accordance with the present invention further has a volume indicating element, and the volume indicating element is adjustably and movably mounted on the main body 10 near the volume barrel 11. When assembling the main body 10, the main body 10 has a rack formed on and protruding from a side of the volume barrel 11, and the volume indicating element is movably mounted on the rack to move upwardly or downwardly relative to the volume barrel 11. In use, the user or the patient can adjust the position of the volume indicating element relative to the volume barrel 11. Then, the user or the patient can train his lung by gradually increasing the training volume, and this can reach a better training effect to the user or the patient.

According to the above-mentioned features and structure relationships of the respiratory training assembly in accordance with the present invention, the respiratory training assembly has the following advantages:

1. The check valve 16 mounted in the mounting recess 142 of the air channel 14 can be used to separate the inspiratory flow path and the expiratory flow path of the respiratory training assembly in accordance with the present invention. Then, the patient will not pollute the floating element 121 during use.

2. It is easy for the patient to know the volume training result in the present invention by viewing the movement of the floating element 121 in the volume barrel 11. The auxiliary indicating device 13 further provides an indicating result of an airflow speed when the patient breathes. The moving speed of the indicating element 133 may help the patient to control and improve the inspiratory stability of using the present invention.

Therefore, the respiratory training assembly in accordance with the present invention can provide multiple functions of training the lung volume and the inspiratory stability to the patient at the same time, and this can increase the rehabilitation speed of the patient.

3. The respiratory training assembly in accordance with the present invention further has the expiratory training device 20, and the expiratory training device 20 can be used to provide an expiratory training to the user or the patient. This enables the respiratory training assembly in accordance with the present invention to achieve the dual training of inspiratory and expiratory effects.

What is claimed is:

1. A respiratory training assembly having a main body, with the main body having:
   a volume barrel partially or completely translucent and having a top, a bottom, an external surface, a chamber, at least one through hole formed through the external surface of the volume barrel near the bottom of the volume barrel and communicating with the chamber of the volume barrel and an air outlet hole formed through the external surface of the volume barrel near the top of the volume barrel and communicating with the chamber of the volume barrel;
   an inspiratory training device movably mounted in the volume barrel and having a floating element mounted movably in the chamber of the volume barrel and being movable upwardly or downwardly relative to the volume barrel;
   an air channel formed on the main body, communicating with the chamber of the volume barrel via the air outlet hole and having an upper end connected to and communicating with the air outlet hole, a lower end, an outlet formed on the lower end of the air channel in the main body and a check valve mounted in the air channel;
   an output-input entrance formed in the main body and communicating with the outlet of the air channel;
   an auxiliary indicating device formed on the main body and having:
      an indicating channel formed on the main body and being in parallel with the volume barrel and having a top end, a bottom end, an internal surface and a drainage branch formed on and protruding downwardly from the top end of the indicating channel and communicating with the indicating channel;

an engaging recess formed in the internal surface of the indicating channel near the bottom end of the indicating channel; and an indicating element movably mounted in the indicating channel, selectively abutting against and holding in the engaging recess and having a top, a bottom, a width and an annular flange formed around the top of the indicating element and selectively abutting against and holding in the engaging recess; and an expiratory training device mounted in the main body between the output-input entrance and the check valve and communicating with the air channel, wherein the expiratory training device has:

an expiratory body being tubular, formed with the main body and communicating with the air channel; and a pressure adjuster mounted movably in the expiratory body to adjust an expired pressure, wherein the expiratory body has:

an external surface;

a forming end formed with the main body and communicating with the outlet of the air channel;

a mounting end;

at least one elongated slot formed axially through the external surface of the expiratory body, with each of the at least one elongated slot having multiple holding recesses formed through the external surface of the expiratory body at intervals and communicating with the at least one elongated slot; and at least one leaking hole formed radially through the external surface of the expiratory body near the forming end of the expiratory body and communicating with the air channel via the forming end of the expiratory body; and with the pressure adjuster having:

a controlling slice movably mounted in the expiratory body near the forming end of the expiratory body;

an elastic element mounted in the expiratory body and abutting against the controlling slice to provide a pushing force to the controlling slice to move toward the forming end of the expiratory body;

an adjusting element movably mounted in the expiratory body, abutting against the elastic element and having an abutting end abutting against the elastic element, with a connecting shaft formed axially on and protruding from the abutting end of the adjusting element opposite to the elastic element, with an external surface and an engaging rod formed radially on and protruding from the external surface of the connecting shaft and having an engaging end extending into the at least one elongated slot and engaging one of the holding recesses of the at least one elongated slot to hold the adjusting element securely with the expiratory body; and a holding cap mounted securely in the mounting end of the expiratory body to hold the adjusting element, the elastic element and the controlling slice mounted securely in the expiratory body.

2. The respiratory training assembly as claimed in claim 1, wherein:

the air channel has a mounting recess formed in the air channel between the outlet and the lower end of the air channel and communicating with the outlet and the air channel; and the check valve is mounted in the mounting recess of the air channel.

3. The respiratory training assembly as claimed in claim 2, wherein the check valve has:

a valve ring mounted in the mounting recess, communicating with the air channel and having a top, an internal surface and at least one hollow section formed in the internal surface of the valve ring and formed through the top of the valve ring;

a floating mount movably mounted in the valve ring and having a top and a retaining board formed annularly on and protruding from the top of the floating mount; and a cover panel mounted in the mounting recess, covered around the top of the valve ring and having at least one gas hole formed through the cover panel and communicating with the air channel, the mounting recess and the at least one hollow section of the valve ring.

4. The respiratory training assembly as claimed in claim 3, further having a handle formed on the main body.

5. The respiratory training assembly as claimed in claim 3, wherein the main body further has:

a rack formed on and protruding from a side of the volume barrel; and a volume indicating element adjustably and movably mounted on the rack of the main body near the volume barrel.

* * * * *